(12) United States Patent
Abe

(10) Patent No.: US 11,599,992 B2
(45) Date of Patent: Mar. 7, 2023

(54) DISPLAY CONTROL APPARATUS, DISPLAY METHOD, AND NON-TRANSITORY STORAGE MEDIUM

(71) Applicant: CANON KABUSHIKI KAISHA, Tokyo (JP)

(72) Inventor: Hiroshi Abe, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 354 days.

(21) Appl. No.: 16/332,562

(22) PCT Filed: Nov. 28, 2017

(86) PCT No.: PCT/JP2017/042615
§ 371 (c)(1),
(2) Date: Mar. 12, 2019

(87) PCT Pub. No.: WO2018/101258
PCT Pub. Date: Jun. 7, 2018

(65) Prior Publication Data
US 2021/0287358 A1    Sep. 16, 2021

(30) Foreign Application Priority Data

Nov. 30, 2016    (JP) .............................. JP2016-233207

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0095* (2013.01); *G06T 5/002* (2013.01); *G06T 15/08* (2013.01); *G06T 2207/30101* (2013.01)

(58) Field of Classification Search
None
See application file for complete search history.

(56) References Cited

U.S. PATENT DOCUMENTS

| 2014/0196544 | A1 | 7/2014 | Wanda |
| 2014/0360271 | A1 | 12/2014 | Fukutani |
| 2015/0043800 | A1 | 2/2015 | Miyasa |
| 2015/0043800 | A1 | 2/2015 | Miyasa |

(Continued)

FOREIGN PATENT DOCUMENTS

| CN | 102639996 A | 8/2012 |
| CN | 103300880 A | 9/2013 |

(Continued)

OTHER PUBLICATIONS

Ge Healthcare: "EchoPAC Software Only v201", Mar. 1, 2015 (Mar. 1, 2015), XP055451274, Retrieved from the IFW on Jul. 20, 2021 (Year: 2015).*

(Continued)

*Primary Examiner* — Vu Le
*Assistant Examiner* — Courtney Joan Nelson
(74) *Attorney, Agent, or Firm* — Canon U.S.A., Inc. IP Division

(57) ABSTRACT

A display control apparatus that performs rendering on volume data generated based on a signal obtained by receiving a photoacoustic wave generated by an object irradiated with light includes a first unit configured to obtain positional information of a surface of the object, a second unit configured to set a region inside the object between a surface located at a first distance from the surface of the object and a surface located at a second distance from the surface of the object as a display region on the basis of the positional information of the surface of the object, and a third unit configured to perform the rendering on the volume data in a manner that the display region and a region except for the display region can be discriminated from each other.

11 Claims, 8 Drawing Sheets

(51) Int. Cl.
 G06T 5/00 (2006.01)
 G06T 15/08 (2011.01)

(56) References Cited

U.S. PATENT DOCUMENTS

| | | | |
|---|---|---|---|
| 2015/0073278 A1 | 3/2015 | Oyama | |
| 2016/0296120 A1* | 10/2016 | Miyasa | ............... A61B 5/0035 |
| 2016/0324423 A1 | 11/2016 | Irisawa et al. | |

FOREIGN PATENT DOCUMENTS

| | | | | |
|---|---|---|---|---|
| CN | 104135936 A | | 11/2014 | |
| CN | 104510495 A | | 4/2015 | |
| CN | 104644127 A | | 5/2015 | |
| CN | 104883965 A | | 9/2015 | |
| DE | 19955690 A1 | * | 6/2000 | ............ G06T 15/08 |
| EP | 2853917 A1 | | 4/2015 | |
| JP | 2010012295 A | | 1/2010 | |
| JP | 4421016 B2 | * | 2/2010 | ........... A61B 8/5238 |
| JP | 2011-183057 A | | 9/2011 | |
| JP | 2013-188461 A | | 9/2013 | |
| JP | 2013233386 A | | 11/2013 | |
| JP | 2014-128319 A | | 7/2014 | |
| JP | 2014530686 A | * | 11/2014 | ............ A61B 5/004 |
| JP | 2015-205136 A | | 11/2015 | |
| JP | 2015-216982 A | | 12/2015 | |
| JP | 2016-27924 A | | 2/2016 | |
| JP | 2016 144523 A | | 8/2016 | |
| KR | 20140140028 A | * | 12/2014 | ............ A61B 5/7225 |

OTHER PUBLICATIONS

Translation of DE-19955690-A1 (Year: 2000).*
Translation of KR-20140140028-A (Year: 2014).*
Machine translation of JP-4421016-B2 (Year: 2010).*
Machine translation of JP2014530686A (Year: 2014).*
Jaken Medical, Inc., "EchoPAC Software Only v201;" GE Healthcare, 2015; https://jakenmedical.com/ge-echopac-v201-software-only.html#product-details-tab-tabfile-attachments. pp. 1-12.
Karin Zell, Jonathan I. Sperl, Stephan Ketzer, Mika W. Vogel, Peter Menzenbach, Reinhard Niessner, and Christoph Haisch; "Optoacoustics Plus Ultrasound May Improve Breast Cancer Detection;" 2007 SPIE; pp. 1-4.
Qi Zhang; Roy Eagleson; Terry M. Peters; "Volume Visualization: A Technical Overview with a Focus on Medical Applications;" Journal of Digital Imaging, vol. 24, No. 4, pp. 640-664.
Ditlef Martens; Odd Helge Gilja; "The EchoPAC-3D Software for 3D Image Analysis," Basic and New Aspects of Gastrointestinal Ultrasonography, Advanced Series in Biomechanics, vol. 3. pp. 304-329.
Wang Jun, Xue Haihong, Chen Guozhen, et al.; "Study on virtual visualization of echocardiography based on isosurface reconstruction;" Shanghai Medical Imaging, vol. 12, No. 4, pp. 243-224 and 329.
Zhou et al.; "Analysis and Processing on the Image Signal of Scanning Laser Acoustic Microscope"; China Academic Journal Electronic Publishing House, vol. 26, No. 5; Oct. 15, 2005.

* cited by examiner

DISPLAY CONTROL APPARATUS, DISPLAY METHOD, AND NON-TRANSITORY STORAGE MEDIUM

TECHNICAL FIELD

The present invention relates to an apparatus that controls display of photoacoustic image data.

BACKGROUND ART

Photoacoustic imaging is one of imaging technologies which with a photoacoustic wave generated from an optical absorber irradiated with light is received, and a spatial distribution of the optical absorber can be imaged. When the photoacoustic imaging is applied to a living body, the optical absorber such as a blood vessel including hemoglobin can be imaged.

PTL 1 describes that a photoacoustic image is generated by using a photoacoustic imaging principle, and rendering is performed on the photoacoustic image to be displayed.

CITATION LIST

Patent Literature

PTL 1: Japanese Patent Laid-Open No. 2011-183057

SUMMARY OF INVENTION

However, in a case where photoacoustic image data includes an unnecessary image based on noise or the like other than an observation target, when rendering is performed on the photoacoustic image data to be displayed, a rendering image having a low diagnostic performance may be generated in some cases.

In view of the above, the present invention provides an apparatus that can display the rendering image in which an influence of the unnecessary image is suppressed even in a case where the photoacoustic image data includes the unnecessary image.

Solution to Problem

An aspect of the present invention relates to a display control apparatus that performs rendering on volume data generated based on a signal obtained by receiving a photoacoustic wave generated by an object irradiated with light, the display control apparatus including a first unit configured to obtain positional information of a surface of the object, a second unit configured to set a region inside the object between a surface located at a first distance from the surface of the object and a surface located at a second distance from the surface of the object as a display region on the basis of the positional information of the surface of the object, and a third unit configured to perform the rendering on the volume data in a manner that the display region and a region except for the display region can be discriminated from each other.

Further features of the present invention will become apparent from the following description of exemplary embodiments with reference to the attached drawings.

DESCRIPTION OF EMBODIMENTS

An aspect of the present invention is an invention related to rendering of photoacoustic image data corresponding to volume data derived from a photoacoustic wave generated by light irradiation. The photoacoustic image data is the volume data representing a three-dimensional spatial distribution of at least one piece of object information such as a generated sound pressure (initial sound pressure), an optical absorption energy density, and an optical absorption coefficient of the photoacoustic wave, a concentration of a material constituting the object (such as an oxygen saturation), and the like.

Figure 1A:
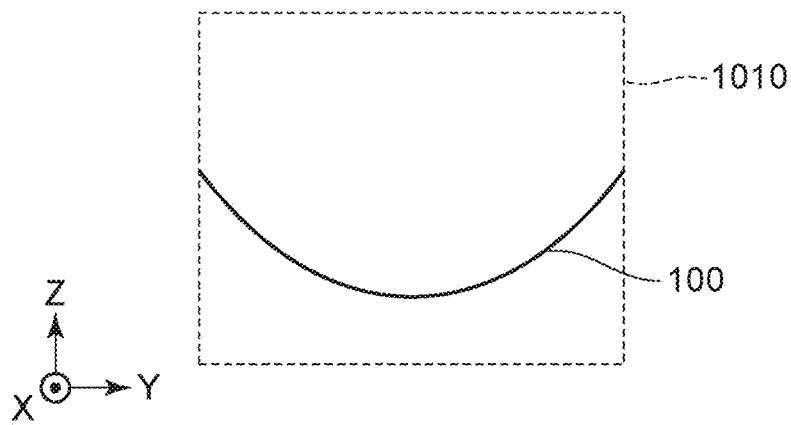
FIG. 1A is a schematic diagram illustrating various regions according to an exemplary embodiment of the present invention.

FIG. 1A is a schematic diagram of the photoacoustic image data as reconstructed volume data in which a rectangular reconstruction region 1010 is set. The photoacoustic image data illustrated in FIG. 1A includes image data of an object 100. The photoacoustic image data illustrated in FIG. 1A is obtained by irradiation of light from a lower direction on paper.

In this case, a light fluence of irradiation light inside the object 100 typically attenuates at an exponential manner from a surface of the object 100. For this reason, typically, the sound pressure of the generated photoacoustic wave tends to decrease as a distance from the surface of the object 100 increases, and a signal-to-noise (S/N) ratio of the photoacoustic image data tends to decrease as the distance from the surface of the object 100 increases. That is, as the distance from the surface of the object 100 increases, an image quality (such as a resolution or a contrast) of a rendering image of the photoacoustic image data also tends to decrease. Although an attenuation degree of the light fluence has an individual difference since a spatial distribution of optical coefficients of the object 100 has an individual difference, a tendency that the image quality of the rendering image decreases as the distance from the surface of the object 100 increases is unchanged.

Figure 1B:
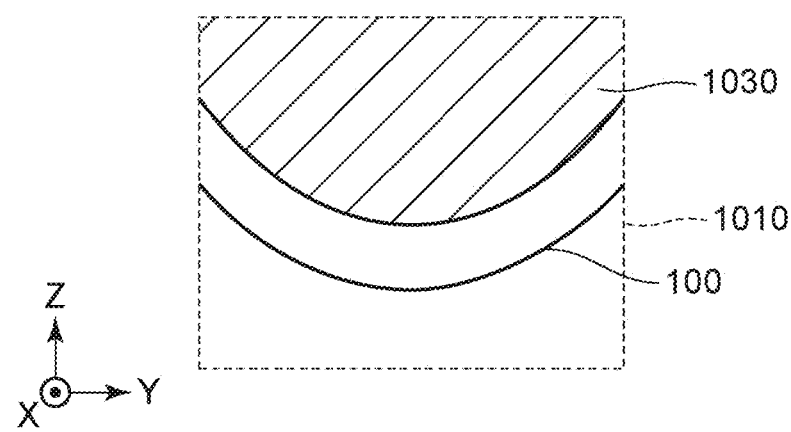
FIG. 1B is a schematic diagram illustrating the various regions according to the exemplary embodiment of the present invention.

In view of the above, the inventor of the present invention has found that rendering is performed on the photoacoustic image data such that a deep region 1030 away from the surface of the object 100 at a predetermined distance or farther is defined as illustrated in FIG. 1B, and the deep region 1030 and the other region can be discriminated from each other. In particular, the inventor of the present invention has found that the rendering is performed on the photoacoustic image data such that the other region is emphasized as compared with the deep region 1030. For example, a transparency of the deep region 1030 is set to be higher than that of the other region, that is, an opacity of the deep region is decreased, and the rendering can be performed such that the other region is emphasized as compared with the deep region 1030. The rendering may also be performed such that the other region is emphasized as compared with the deep region 1030 by adjusting a luminance. The rendering can also be performed such that the region except for the deep region is emphasized by excluding the deep region 1030 from a rendering target. It should be noted that the rendering may be performed such that a region except for the object 100 is not emphasized by increasing the transparency, decreasing the luminance, excluding the region from the rendering target, or the like. Hereinafter, a phrase "the region can be discriminated" refers to a state in which the region can be independently visually recognized.

When the rendering is performed on the photoacoustic image data as described above, it is possible to display the rendering image in which an influence from the region where reaching light fluences are low and the image quality decreases is suppressed. As a result, a user such as a doctor can check the rendering image where the high image quality region is selectively (preferentially) displayed to perform a diagnosis, and a diagnosis performance is improved.

Figure 1C:
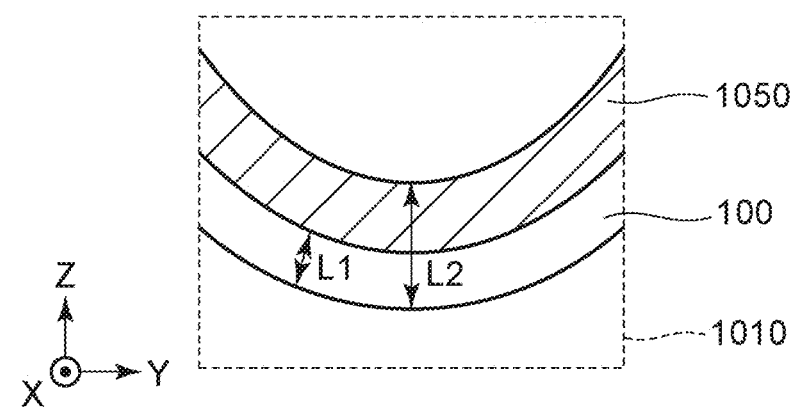
FIG. 1C is a schematic diagram illustrating the various regions according to the exemplary embodiment of the present invention.

In a case where an inner region with respect to the surface of the object 100 is desired to be observed, a display region 1050 may be defined as illustrated in FIG. 1C, and the rendering may be performed on the photoacoustic image data such that the display region 1050 and the other region can be distinguished from each other. For example, the rendering may be performed on the photoacoustic image data such that the display region 1050 is more emphasized than the other region. That is, a region between a surface away from the surface of the object 100 by a first distance L1 and a surface away from the surface of the object 100 by a second distance L2 may be defined as the display region 1050. It should be noted that the first distance L1 may be set as 0, and the surface of the object 100 may be set as one surface of the display region 1050.

When the rendering is performed as described above, it is possible to display the rendering image in which the influence from not only the region with the low light fluences but also the region in the vicinity of the surface of the object 100 which is not the observation target is suppressed. For this reason, the user such as the doctor can check the image in which the region desired to be observed also corresponding to the high image quality region are selectively (preferentially) subjected to the rendering to perform the diagnosis, and the diagnosis performance is improved.

Light fluence distribution information (spatial distribution of the light fluences) inside the object 100 may be obtained, and a region where the light fluences are within a predetermined range (for example, values higher than a predetermined threshold) may be defined as the display region. Furthermore, a region overlapped by the region where the light fluences are within the predetermined range (for example, the values higher than the predetermined threshold) and the display region 1050 illustrated in FIG. 1C may be defined as the display region.

Hereinafter, an exemplary embodiment of the present invention will be described with reference to the drawings. It should be noted however that dimensions, materials, and shapes of components which will be described below, those relative positions, and the like are to be appropriately changed depending on the configurations and various conditions of the apparatus to which the exemplary embodiment of the present invention is applied, and are not intended to limit the scope of the present invention to the following descriptions.

Hereinafter, a configuration of a photoacoustic apparatus according to the present exemplary embodiment and an information processing method will be described.

Figure 2:
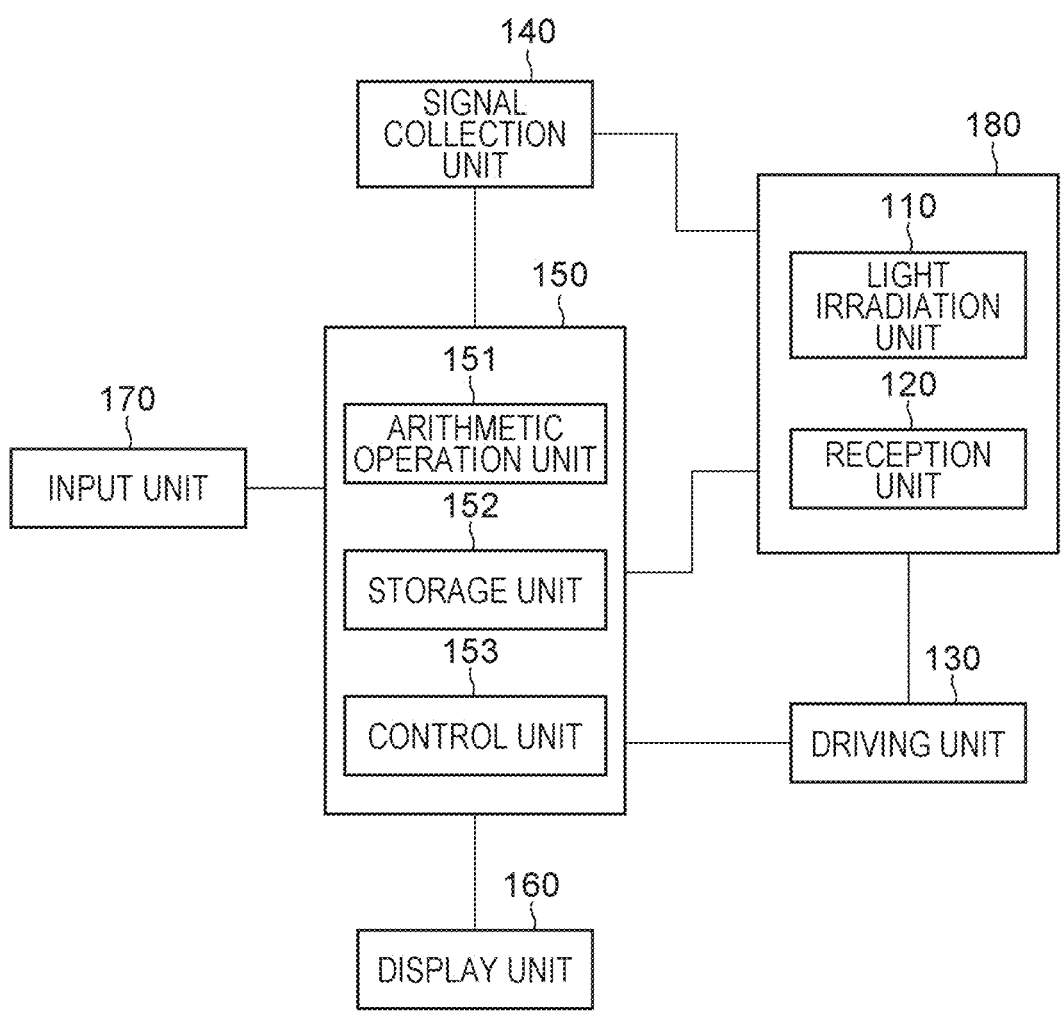
FIG. 2 is a block diagram illustrating a photoacoustic apparatus according to the present exemplary embodiment.

According to the present exemplary embodiment, an example using a photoacoustic apparatus will be described. The configuration of the photoacoustic apparatus according to the present exemplary embodiment will be described with reference to FIG. 2. FIG. 2 is a schematic block diagram of the entirety of the photoacoustic apparatus. The photoacoustic apparatus according to the present exemplary embodiment includes a probe 180 including a light irradiation unit 110 and a reception unit 120, a driving unit 130, a signal collection unit 140, a computer 150, a display unit 160, and an input unit 170.

Figure 3A:
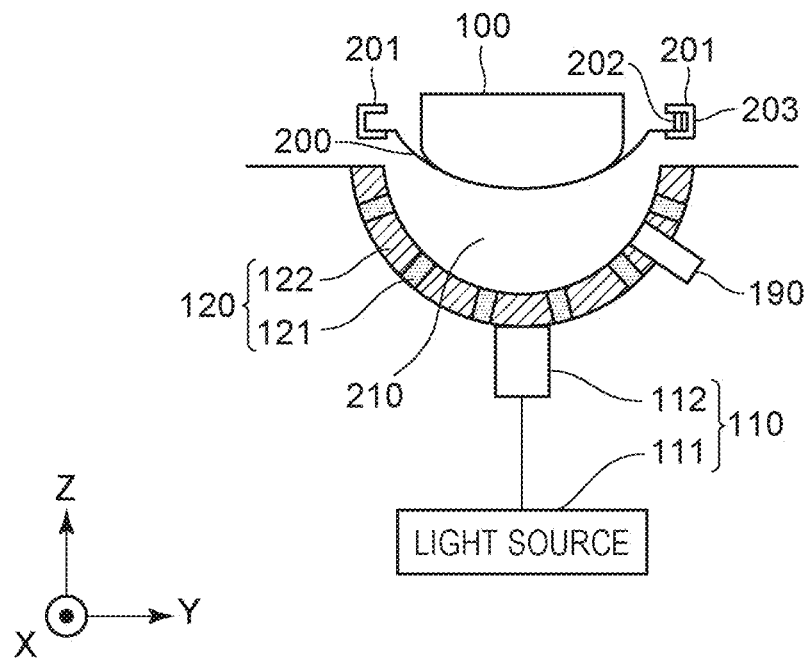
FIG. 3A is a schematic diagram illustrating a probe according to the present exemplary embodiment.
Figure 3B:
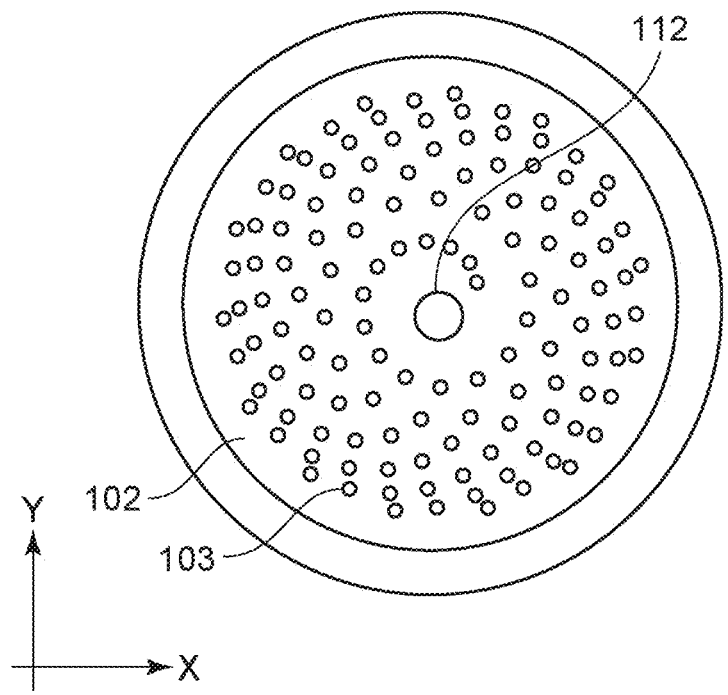
FIG. 3B is a schematic diagram illustrating the probe according to the present exemplary embodiment.

FIGS. 3A and 3B are schematic diagrams of the probe 180 according to the present exemplary embodiment. A measurement object is the object 100. The driving unit 130 drives the light irradiation unit 110 and the reception unit 120 and performs mechanical scanning. The light irradiation unit 110 irradiates the object 100 with light, and an acoustic wave is generated in the object 100. The acoustic wave generated by a photoacoustic effect derived from the light is also referred to as a photoacoustic wave. The reception unit 120 outputs an electric signal (photoacoustic signal) as an analog signal when the photoacoustic wave is received.

The signal collection unit 140 converts the analog signal output from the reception unit 120 into a digital signal to be output to the computer 150. The computer 150 stores the digital signal output from the signal collection unit 140 as signal data derived from an ultrasonic wave or the photoacoustic wave.

The computer 150 generates volume data (photoacoustic image) representing information (object information) related to the object 100 by performing signal processing on the stored digital signal. The computer 150 also performs rendering on the obtained volume data to be output to the display unit 160. The display unit 160 displays the rendering image of the volume data. The doctor acting as the user can perform the diagnosis by checking the rendering image displayed on the display unit 160. The display image is saved in a memory in the computer 150, a data management system connected to a modality by a network, or the like on the basis of a saving instruction from the user or the computer 150.

The computer 150 also performs driving control on the components included in the photoacoustic apparatus. The display unit 160 may also display a graphical user interface (GUI) or the like in addition to the image generated by the computer 150. The input unit 170 is configured such that the user can input information. The user can perform operations such as measurement start and end and the saving instruction of the generated image by using the input unit 170.

Hereinafter, details of the respective components of the photoacoustic apparatus according to the present exemplary embodiment will be described.

Light Irradiation Unit 110

The light irradiation unit 110 includes a light source 111 that emits light and an optical system 112 that guides the light emitted from the light source 111 to the object 100. It should be noted that the light includes pulse light such as a so-called rectangular wave or chopping wave.

A pulse width of the light emitted from the light source 111 may be a pulse width larger than or equal to 1 ns and smaller than or equal to 100 ns. A wavelength in a range between approximately 400 nm to approximately 1600 nm may be set as a wavelength of the light. A wavelength (which is higher than or equal to 400 nm and lower than or equal to 700 nm) at which absorption in the blood vessel is high may be used in a case where imaging of the blood vessel is performed at a high resolution. Light at a wavelength (which is higher than or equal to 700 nm and lower than or equal to 1100 nm) at which absorption in a background tissue (such as water or fat) of the living body is typically low may be used in a case where imaging of a deep part of the living body is performed.

A laser or a light emitting diode can be used as the light source 111. When measurement is performed by using lights at a plurality of wavelengths, a light source that can change the wavelength may also be used. It should be noted that, in a case where the object is irradiated with the plurality of wavelengths, a plurality of light sources that generate lights having mutually different wavelengths can be prepared, and the lights are alternately emitted from the respective light sources. Even in a case where the plurality of light sources are used, those light sources are collectively represented as the light source. Various lasers including a solid-state laser, a gas laser, a dye laser, and a semiconductor laser can be used as the laser. For example, a pulse laser such as an Nd:YAG laser and an alexandrite laser may be used as the light source. In addition, a Ti:sa laser or an optical parametric oscillator (OPO) using Nd:YAG laser light as exciting light laser may be used as the light source. Moreover, a flash lamp or a light emitting diode may be used as the light source 111. Furthermore, a microwave source may be used as the light source 111.

An optical element such as a lens, a mirror, or an optical fiber can be used as the optical system 112. In a case where a breast or the like is set as the object 100, to perform the irradiation by widening a beam diameter of the pulse light, a light outgoing part of the optical system 112 may be constituted by a diffusing plate or the like that diffuses the light. On the other hand, to increase the resolution, the light outgoing part of the optical system 112 may be constituted by a lens or the like, and the irradiation may be performed while the beam is focused in a photoacoustic microscope.

It should be noted that the light irradiation unit 110 may directly irradiate the object 100 with light from the light source 111 without the provision of the optical system 112.

Reception Unit 120

The reception unit 120 includes transducers 121 that output an electric signal when the acoustic wave is received and a supporting member 1:22 that supports the transducers 121. A transmission unit that transmits an acoustic wave may be set as the transducer 121. A transducer serving as a reception unit and the transducer serving as the transmission unit may be a single (common) transducer or may also be separate components.

A piezo-ceramic material represented by lead zirconate titanate (PZT), a polymer piezoelectric membrane material represented by poly vinylidene-fluoride (PVDF), or the like can be used as a member constituting the transducer 121. An element other than a piezoelectric element may also be used. For example, a capacitive micromachined ultrasonic transducer (CMUT), a transducer using a Fabry-Perot interferometer, or the like can be used. It should be noted that any transducer may be adopted as long as the transducer can output the electric signal when the acoustic wave is received. The signal obtained by the transducer is a time-resolved signal. That is, an amplitude of the signal obtained by the transducer represents a value based on a sound pressure received by the transducer at each time (for example, a value in proportion to the sound pressure).

A frequency component constituting the photoacoustic wave is typically 100 KHz to 100 MHz, and it is possible to adopt an element that can detect these frequencies as the transducer 121.

The supporting member 122 may be formed of a metallic material having a high mechanical strength or the like. A surface on a side of the object 100 of the supporting member 122 may be processed to have a mirror surface or realize light scattering such that much irradiation light enters the object. According to the present exemplary embodiment, the supporting member 122 has a shape of a hemispherical enclosure and is constituted such that the plurality of transducers 121 can be supported on the hemispherical enclosure. In this case, directional axes of the transducers 121 arranged in the supporting member 122 converge in the vicinity of the center of curvature of the hemispherical enclosure. An image quality in the vicinity of the center of curvature is increased when the imaging is performed by using the signals output from the plurality of transducers 121. It should be noted that the supporting member 122 may adopt any configuration as long as the supporting member 122 can support the transducers 121. The plurality of transducers may be disposed and arranged in a plane or a curved-surface such as a so-called 1 D array, 1.5 D array, 1.75 D array, or 2 D array in the supporting member 122. The plurality of transducers 121 are equivalent to a plurality of reception units.

The supporting member 122 may also function as a container that retains an acoustic matching material 210. That is, the supporting member 122 may be constituted by a container that arranges the acoustic matching material 210 between the transducer 121 and the object 100.

The reception unit 120 may include an amplifier that amplifies a time-series analog signal output from the transducer 121. The reception unit 120 may also include an analog-to-digital converter that converts the time-series analog signal output from the transducer 121 into a time-series digital signal. That is, the reception unit 120 may include the signal collection unit 140 which will be described below.

It should be noted that the transducers 121 may be ideally arranged so as to surround the object 100 from the entire circumference such that the acoustic waves can be detected at various angles. It should be noted however that, in a case where the transducers are not arranged so as to surround the object 100 from the entire circumference because the object 100 is large, the transducers may be arranged on the hemispherical supporting member 122 to substantially establish a state in which the object 100 is surrounded from the entire circumference.

It should be noted that the arrangement and the number of the transducers and the shape of the supporting member may be optimized in accordance with the object, and any type of the reception unit 120 can be adopted with regard to the exemplary embodiment of the present invention.

A space between the reception unit 120 and the object 100 is filled with a medium with which the photoacoustic wave propagates. A material in which the acoustic wave can propagate, acoustic characteristics are matched on an interface between the object 100 and the transducer 1:21, and transmittance of the photoacoustic wave is high as much as possible is adopted as this medium. For example, water, ultrasonic gel, or the like may be adopted as this medium.

FIG. 3A is a lateral view of the probe 180, and FIG. 3B is a top view of the probe 180 (viewed from an upward direction on paper in FIG. 3A). The probe 180 according to the present exemplary embodiment illustrated in FIG. 2 includes the reception unit 120 in which the plurality of transducers 121 are three-dimensionally arranged in the hemispherical supporting member 122 having openings. The light outgoing part of the optical system 112 is arranged in a bottom part of the supporting member 122 in the probe 180 illustrated in FIG. 2.

According to the present exemplary embodiment, as illustrated in FIG. 2, while the object 100 is in contact with a holding part 200, a shape of the object 100 is maintained. According to the present exemplary embodiment, in a case where the object 100 is the breast, a mode is presumed in which a bunk that supports an examinee in a prone position is provided with an opening for inserting the breast, and the breast draping in a vertical direction from the opening is measured.

A space between the reception unit 120 and the holding part 200 is filled with a medium (the acoustic matching material 210) in which the photoacoustic wave can propagate. A material in which the acoustic wave can propagate, the acoustic characteristics are matched on the interface between the object 100 and the transducer 121, and the transmittance of the photoacoustic wave is high as much as possible is adopted as this medium. For example, water, ultrasonic gel, or the like may be adopted as this medium.

The holding part 200 as a holding unit is used for holding the shape of the object 100 during the measurement. While the holding part 200 holds the object 100, a movement of the object 100 can be suppressed, and the position of the object 100 can be kept in the holding part 200. A resin material such as polycarbonate, polyethylene, or polyethylene terephthalate can be used as a material of the holding part 200.

The holding part 200 is preferably formed of a material having a firmness to such an extent that the object 100 can be held. The holding part 200 may be formed of a material through which the light used in the measurement transmits. The holding part 200 may be formed of a material in which an impedance is at a comparable level with that of the object 100. In a case where on object having a curvature of the breast or the like is set as the object 100, the holding part 200 molded to have a concave shape may also be adopted. In this case, the object 100 can be inserted into a concave part of the holding part 200.

The holding part 200 is attached to a fitting part 201. The fitting part 201 may be constituted in a manner that a plurality of types of the holding parts 200 can be replaced in accordance with the size of the object. For example, the fitting part 201 may also be constituted in a manner that holding parts having different radii of curvature, centers of curvature, or the like can be replaced.

A tag 202 in which information of the holding part 200 is registered may be installed in the holding part 200. For example, it is possible to register information such as the radius of curvature or the center of curvature of the holding part 200, acoustic velocity, or an identification ID in the tag 202. The information registered in the tag 202 is read out by a reading unit 203 to be transferred to the computer 150. To easily read the tag 202 when the holding part 200 is attached to the fitting part 201, the reading unit 203 may be installed in the fitting part 201. For example, the tag 202 is a barcode, and the reading unit 203 is a barcode reader.

Driving Unit 130

The driving unit 130 is a part that changes a relative position of the object 100 and the reception unit 120. According to the present exemplary embodiment, the driving unit 130 is an apparatus that moves the supporting member 122 in an XY direction and is an electrically-driven XY stage to which a stepping motor is mounted. The driving unit 130 includes a motor such as the stepping motor that generates driving force, a driving mechanism that transmits the driving force, and a positional sensor that detects positional information of the reception unit 120. A lead screw mechanism, a link mechanism, a gear mechanism, an oil pressure mechanism, or the like can be used as the driving mechanism. A potentiometer or the like using an encoder, a variable resistor, or the like can be used as the positional sensor.

It should be noted that the driving unit 130 may not only change the relative position of the object 100 and the reception unit 120 in the XY direction (two dimensions) but also change one-dimensionally or three-dimensionally. A movement path may be two-dimensionally scanned in a spiral shape or a line and space manner, and furthermore, the movement path may be three-dimensionally inclined along a body surface. In addition, the probe 180 may be moved so as to keep a constant distance from the surface of the object 100. At this time, the driving unit 130 may measure the movement amount of the probe by monitoring the number of revolutions of the motor or the like.

It should be noted that the driving unit 130 may fix the reception unit 120 and move the object 100 as long as the relative position of the object 100 and the reception unit 120 can be changed. A configuration in which the object 100 is moved by moving the holding part that holds the object 100 or the like is conceivable in a case where the object 100 is moved. Both the object 100 and the reception unit 120 may also be moved.

The driving unit 130 may continuously move the relative position or may move the relative position by a step and repeat manner. The driving unit 130 may be an electrically-driven stage that moves the relative position on a programmed track or a manually-operated stage. That is, the photoacoustic apparatus may be of a hand-held type in which the user performs the operation by holding the probe 180 without the provision of the driving unit 130.

In addition, according to the present exemplary embodiment, the driving unit 130 simultaneously drives the light irradiation unit 110 and the reception unit 120 to perform the scanning, but only the light irradiation unit 110 may be driven, and also only the reception unit 120 may be driven.

Signal Collection Unit 140

The signal collection unit 140 includes an amplifier that amplifies the electric signal corresponding to the analog signal output from the transducer 121 and the A/D converter that converts the analog signal output from the amplifier into the digital signal. The signal collection unit 140 may be constituted by a field programmable gate array (FPGA) chip or the like. The digital signal output from the signal collection unit 140 is stored in a storage unit 152 in the computer 150. The signal collection unit 140 is also referred to as a data acquisition system (DAS). The electric signal in the present specification is a concept including both of the analog signal and the digital signal. It should be noted that the signal collection unit 140 may be connected to a light detection sensor attached to the light outgoing part of the light irradiation unit 110 and start processing in synchronism with the light emitted from the light irradiation unit 110 as a trigger. In addition, the signal collection unit 140 may start the processing in synchronism with an instruction issued by using a freeze bottom or the like as a trigger.

Computer 150

The computer 150 serving as a display control apparatus includes an arithmetic operation unit 151, the storage unit 152, and a control unit 153. Functions of the respective configurations will be described when a processing flow will be described.

Units realizing an arithmetic operation function as the arithmetic operation unit 151 can be constituted by a processor such as a CPU or a graphics processing unit (GPU) or an arithmetic operation circuit such as a field programmable gate array (FPGA) chip. These units may be constituted by not only a single processor or arithmetic operation circuit but also a plurality of processors or arithmetic operation circuits. The arithmetic operation unit 151 may receive various parameters such as the object acoustic velocity or the configuration of the holding part from the input unit 170 and process the reception signal.

The storage unit 152 can be constituted by a read only memory (ROM) or a non-transitory storage medium such as a magnetic disc or a flash memory. The storage unit 152 may also be a volatile medium such as a random access memory (RAM). It should be noted that the storage medium that stores the program is the non-transitory storage medium. It should be noted that the storage unit 152 may be not only constituted by a single storage medium but also constituted by a plurality of storage media.

The storage unit 152 can save image data indicating the photoacoustic image generated by the arithmetic operation unit 151 by a method which will be described below.

The control unit 153 is constituted by an arithmetic operation element such as a CPU. The control unit 153 controls operations of the respective components of the photoacoustic apparatus. The control unit 153 may receive instruction signals based on various operations such as measurement start from the input unit 170 and control the respective components of the photoacoustic apparatus. The control unit 153 also reads out program codes stored in the storage unit 152 and controls actions of the respective components of the photoacoustic apparatus.

The computer 150 may be a dedicatedly designed work station. Respective configurations of the computer 150 may be constituted by different hardware components. In addition, at least part of the configurations of the computer 150 may be constituted by a single piece of hardware.

Figure 4:
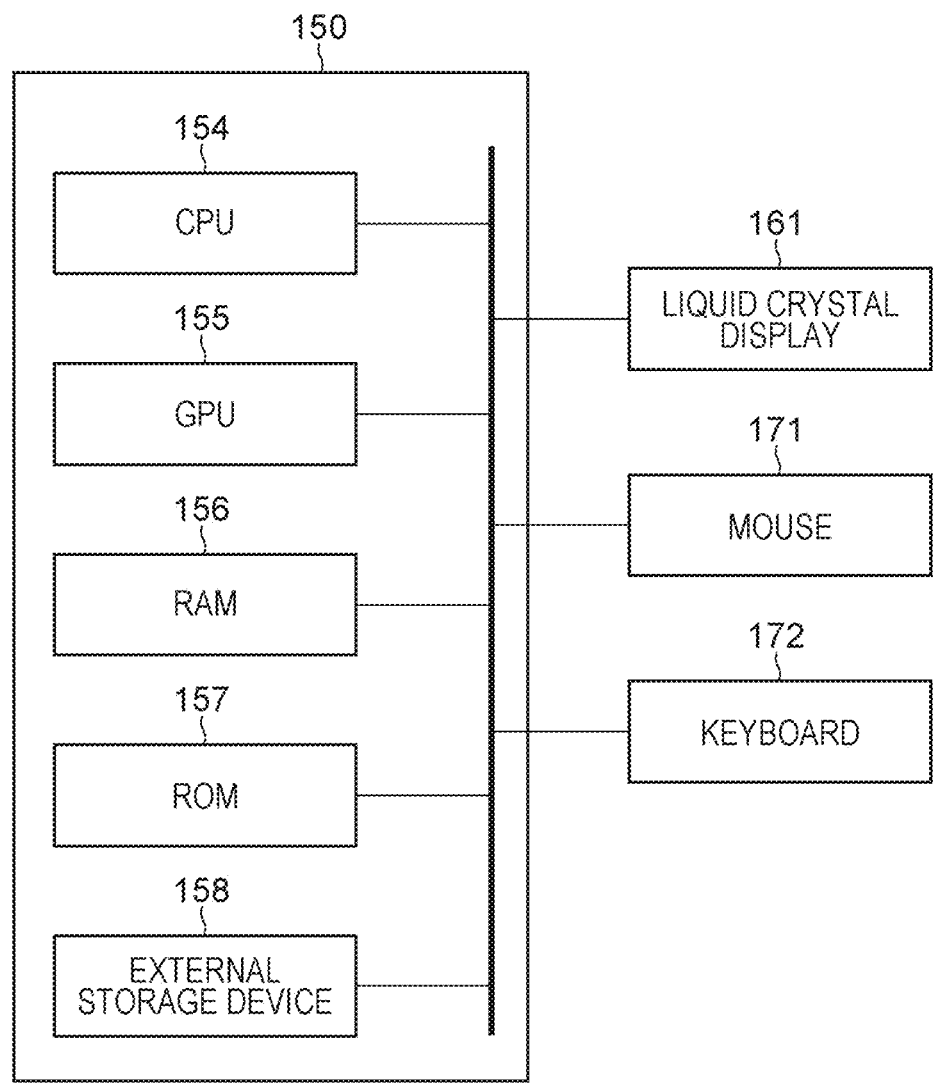
FIG. 4 is a block diagram illustrating a computer and its surrounding configuration according to the present exemplary embodiment.

FIG. 4 illustrates a specific configuration example of the computer 150 according to the present exemplary embodiment. The computer 150 according to the present exemplary embodiment is constituted by a CPU 154, a GPU 155, a RAM 156, a ROM 157, and an external storage device 158. A liquid crystal display 161 functioning as the display unit 160 and a mouse 171 and a keyboard 172 functioning as the input unit 170 are connected to the computer 150.

The computer 150 and the plurality of transducers 121 may be provided by a configuration of being contained in a common casing. It should be noted however that the computer contained in the casing may perform part of the signal processing, and a computer installed outside the casing may perform the rest of the signal processing. In this case, the computers installed inside and outside the casing can be collectively referred to as the computer according to the present exemplary embodiment. That is, it is sufficient even when hardware components constituting the computer are not contained in the single casing.

Display Unit 160

The display unit 160 is a display such as a liquid crystal display, an organic electro luminescence (EL) FED, a spectacle display, or a head mounted display. The display unit 160 is an apparatus that displays an image based on the object information or the like obtained by the computer 150, a numeric value of a specific position, or the like. The display unit 160 may display a GUI for operating the image or the apparatus. It should be noted that, when the object information is displayed, image processing (such as adjustment of the luminance value) may be performed in the display unit 160 or the computer 150 before the display is performed. The display unit 160 may be provided separately in addition to the photoacoustic apparatus. The computer 150 can transmit the photoacoustic image data to the display unit 160 in a wired or wireless manner.

Input Unit 170

An operation console can be adopted as the input unit 170. The operation console is constituted by a mouse, a keyboard, or the like that can be operated by the user. The display unit 160 may be constituted by a touch panel, and the display unit 160 can be used as the input unit 170.

The input unit 170 may be constituted such that information of a position or a depth to be desired to be observed or the like can be input. As an input method, a numeric value may be input, or an input operation can be performed by operating a slider bar. The image to be displayed on the display unit 160 may be updated in accordance with the input information. As a result, the user can set appropriate parameters by checking at the image generated by the parameters determined by its own operation.

It should be noted that the respective components of the photoacoustic apparatus may be constituted as individual apparatuses or may be constituted as an integrated single apparatus. A configuration as a single apparatus may also be adopted in which at least part of the components of the photoacoustic apparatus is integrated.

The information transmitted and received between the respective components of the photoacoustic apparatus is exchanged in a wired or wireless manner.

Object 100

The object 100 will be described below although the object 100 does not constitute the photoacoustic apparatus. The photoacoustic apparatus according to the present exemplary embodiment can be used for a purpose of a diagnosis on malignant tumor, blood vessel disease, or the like of a human being or an animal, follow-up of a chemical treatment, or the like. Therefore, a living body, specifically, a target region of the diagnosis such as a human or animal breast, respective organs, a network of vessels, a head region, a neck region, an abdominal region, or four limbs including fingers and toes is presumed as the object 100. For example, when a human body is the measurement object, a newborn blood vessel formed in the vicinity of a blood vessel or tumor containing a large amount of oxyhemoglobin or deoxyhemoglobin or the like may be set as the target of the optical absorber. Plaque of a carotid wall or the like may also be set as the target of the optical absorber. In addition, pigment such as methylene blue (MB) or indocyanine green (ICG), fine gold particles, or a material where those materials are accumulated or a chemically modified material introduced from the outside may be set as the optical absorber.

Figure 5:
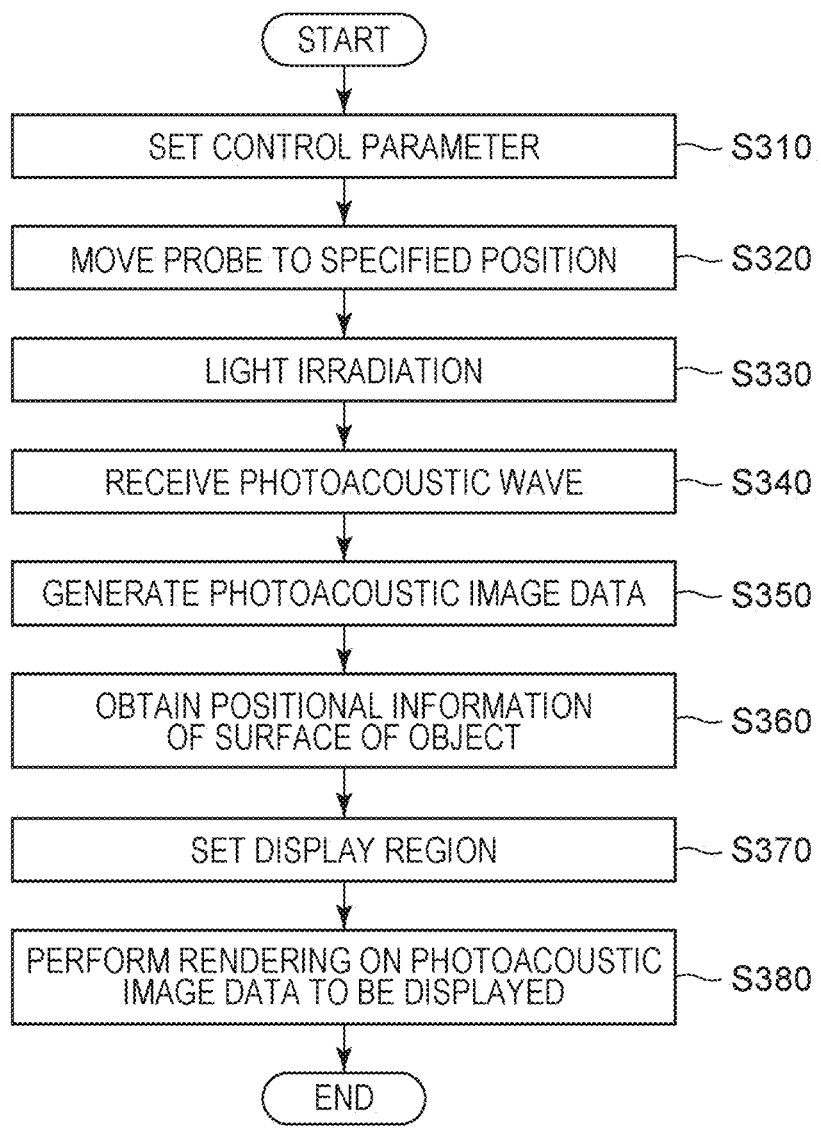
FIG. 5 is a flow chart illustrating a display method according to the present exemplary embodiment.

Next, a display method including information processing according to the present exemplary embodiment will be described with reference to FIG. 5. It should be noted that respective steps are executed while the computer 150 controls the operations of the components of the photoacoustic apparatus.

S310: Step of Setting Control Parameter

The user uses the input unit 170 to specify a control parameter such as an irradiation condition (repetition frequency or wavelength) of the light irradiation unit 110 which is used for obtaining the object information or a position of the probe 180. The computer 150 sets the control parameter determined on the basis of the instruction of the user.

S320: Step of Moving Probe to Specified Position

The control unit 153 causes the driving unit 130 to move the probe 180 to a specified position on the basis of the control parameter specified in step S310. In a case where the imaging is specified in a plurality of positions in step S310, first, the driving unit 130 moves the probe 180 to an initial specified position. It should be noted that the driving unit 130 may move the probe 180 to a previously programmed position when a start instruction for measurement is issued. It should be noted that the user may hold the probe 180 to be moved to a desired position in a case where the photoacoustic apparatus is of the hand-held type.

S330: Step of Performing Light Irradiation

The light irradiation unit 110 irradiates the object 100 with light on e basis of the control parameter specified in step S310.

The object 100 is irradiated with the light generated from the light source 111 via the optical system 112 as the pulse light. Subsequently, the pulse light is absorbed inside the object 100, and the photoacoustic wave is generated by the photoacoustic effect. The light irradiation unit 110 transmits a synchronization signal to the signal collection unit 140 along with the transmission of the pulse light.

S340: Step of Receiving Photoacoustic Wave

The signal collection unit 140 starts signal collection when the synchronization signal transmitted from the light irradiation unit 110 is received. That is, the signal collection unit 140 performs amplification and AD conversion of the analog electric signal derived from the acoustic wave which is output from the reception unit 120 to generate the amplified digital electric signal to be output to the computer 150. The computer 150 saves the signal transmitted from the signal collection unit 140 in the storage unit 152. In a case where the imaging is specified in a plurality of scanning positions in step S301, the steps S320 to S340 are repeatedly executed in the specified scanning positions, and the pulse light irradiation and the generation of the digital signal derived from the acoustic wave are repeated.

S350: Step of Generating Photoacoustic Image Data

The arithmetic operation unit 151 in the computer 150 generates the photoacoustic image data as the volume data based on signal data stored in the storage unit 152 and saves the photoacoustic image data in the storage unit 152. Any techniques such as a time domain reverse projection method, a Fourier domain reverse projection method, or a model base method (repeated operation method) may be adopted as a reconstruction algorithm for converting the signal data into the three-dimensional volume data. For example, the time domain reverse projection method includes universal back-projection (UBP), filtered back-projection (FBP), phasing addition (delay-and-sum), or the like. For example, the arithmetic operation unit 151 may adopt a UBP method represented by Expression (1) as the reconstruction technology for obtaining a three-dimensional spatial distribution of a generated sound pressure (initial sound pressure) of the acoustic wave as the photoacoustic image data.

[Math. 1]

$$p_0(r_0) = \frac{\sum_i^N b\left(r_i, t = \frac{|r_i - r_0|}{c}\right) \cdot \Delta\Omega_i}{\sum_i^N \Delta\Omega_i} \quad (1)$$

$$b(r, t) = 2p(r, t) - 2t\frac{\partial p(r, t)}{\partial t}$$

Where $r_0$ denotes a positional vector indicating a position for performing reconstruction (also referred to as a reconstruction position or a position of interest), $p_0(r_0, t)$ denotes an initial sound pressure in the position for performing the reconstruction, and c denotes the acoustic velocity of a propagation path. $\Delta\Omega_i$ denotes a solid angle viewing the i-th transducer 121 from the position for performing the reconstruction, and N denotes the number of the transducers 121 used for the reconstruction. Expression (1) represents performance of phasing addition (reverse projection) by carrying out processing such as differentiation on reception signals $p(r_i, t)$ and applying weighting of the solid angle to those. Herein, t in Expression (1) denotes a time (propagation time) for the photoacoustic wave to propagate through an acoustic ray between the position of interest and the transducer 121. It should be noted that arithmetic operation processing may also be performed in a calculation of b t). For example, the arithmetic operation processing includes frequency filtering (low-pass, high-pass, band-pass, or the like), deconvolution, envelope demodulation, wavelet filtering, or the like.

The arithmetic operation unit 151 may also obtain absorption coefficient distribution information by calculating the light fluence distribution inside the object 100 of the light with which the object 100 is irradiated and dividing an initial sound pressure distribution by the light fluence distribution. In this case, the absorption coefficient distribution information may be obtained as the photoacoustic image data. In addition, steps in S330 and S340 may be executed by using lights at a plurality of wavelengths, and the arithmetic operation unit 151 may obtain the absorption coefficient distribution information corresponding to each of the lights at the plurality of wavelengths. The arithmetic operation unit 151 may obtain spatial distribution information of a concentration of a material constituting the object 100 as spectroscopic information as the photoacoustic image data on the basis of the absorption coefficient distribution information corresponding to each of the lights at the plurality of wavelengths.

S360: Step of Obtaining Positional Information of Object Surface

The computer 150 serving as a first unit obtains positional information of the surface of the object 100 to be saved in the storage unit 152. The positional information may be coordinates of the surface themselves or may also be information representing the position of the surface by a function.

For example, the computer 150 may receive positional information of the surface of the object 100 obtained by an optical three-dimensional camera and obtain the positional information of the surface of the object 100. The computer 150 may also obtain the positional information of the surface of the object 100 on the basis of the three-dimensional image data of the object 100 imaged by the optical three-dimensional camera or the other modality (such as the ultrasonic diagnosis apparatus, the CT, or the MRI). In this case, the computer 150 may obtain the position information of the surface of the object 100 by performing image processing such as edge detection processing on the three-dimensional image data of the object 100. It should be noted that the optical three-dimensional camera or the other modality may be an apparatus integrated with the photoacoustic apparatus according to the present exemplary embodiment or may be a separate apparatus.

The computer 150 may obtain the positional information of the surface of the object 100 on the basis of the photoacoustic image data obtained in S350. In this case too, the computer 150 may obtain the positional information of the surface of the object 100 by performing the image processing such as the edge detection processing on the photoacoustic image data. For example, after a smoothing filter such as Gaussian is applied to the photoacoustic image data, the computer 150 can define a quasi isosurface in the photoacoustic image data after the smoothing as the surface of the object 100. That is, a surface continuously having substantially equal values in the volume data can be defined as the surface of the object 100. It should be noted that not only a surface constituted by completely equal values in the photoacoustic image data after the smoothing but also a surface in which a variation in the image values is within a predetermined range may be defined as the quasi isosurface. With regard to a curved surface or a curved line corresponding to a candidate of the surface of the object 100, an order, a coefficient, or the like may be previously set in accordance with the shape of the object 100 to be imaged. As a result, it is possible to reduce processing time used for defining the surface of the object 100.

In addition, the computer 150 may perform rendering on the photoacoustic image data obtained in S350 to be displayed on the display unit 160 and obtain the positional information of the surface of the object 100 by using the displayed rendering image. For example, when the user operates the input unit 170, a plurality of positions assumed to be the surface of the object 100 are clicked in the rendering image. Subsequently, the computer 150 may interpolate and connect those positions to define the surface and obtain the positional information of the surface of the object 100. In addition, when the user directly inputs coordinates of the positions assumed to be the surface of the object 100 while the rendering image is checked, the computer 150 may obtain the positional information of the surface of the object 100.

S370: Step of Setting Display Region

The computer 150 serving as a second unit sets a region with the high reaching light fluences as the display region on the basis of the positional information of the surface of the object 100 obtained in S360. Information indicating the display region is saved in the storage unit 152. The information indicating the display region may be in any form of representation such as a coordinate group corresponding to the display region or a function representing the display region as long as the display region can be represented.

For example, as illustrated in FIG. 1B, the computer 150 sets the deep region 1030 away from the surface of the object 100 by a predetermined distance or farther on the basis of the positional information of the surface of the object 100. Furthermore, the computer 150 sets a region except for the deep region 1030 as the display region. As described above, the light fluence of the light propagating through the inside of the object 100 typically tends to attenuate as the distance from the surface of the object 100 increases. In addition, the distance from the surface of the object 100 at which the image quality of the rendering image is below a desired reference can be estimated on the basis of Lambert-Beer's law or the like represented by Expression (2).

$$I = I_0 \exp(-kr) \quad (2)$$

$I_0$ denotes an incidence intensity of the irradiation light, k denotes an effective attenuation coefficient, r denotes a distance from the surface of the object 100, and I denotes an intensity of the irradiation light at the distance r.

The computer 150 may determine the distance from the surface of the object 100 to the deep region 1030 on the basis of the incidence intensity of the irradiation light or the effective attenuation coefficient (or a parameter such as an absorption coefficient, a scattering coefficient, or an anisotropic, coefficient for determining effective attenuation). The intensity of the irradiation light specified by the user using the input unit 170 or the effective attenuation coefficient (or the parameter such as the absorption coefficient, the scattering coefficient, or the anisotropic coefficient for determining the effective attenuation may also be input. The user may also input the distance from the surface of the object 100 to the deep region 1030 by using the input unit 170. The computer 150 may determine the distance from the surface of the object 100 to the deep region 1030 or the display region in accordance with the information input by the user. The computer 150 may also exclude a region except for the object 100 from the display region on the basis of the positional information of the surface of the object 100.

The computer 150 may set a region between the surface away from the surface of the object 100 by the first distance L1 and the surface away from the surface of the object 100 by the second distance L2 as the display region as illustrated in FIG. 1C. The user may also input information for determining a depth corresponding to a starting point of the display region (first distance L1) and a depth corresponding to an ending point (second distance L2) of the display region by using the input unit 170. The computer 150 may determine the display region in accordance with the information input by the user. In addition, the computer 150 may read out the information indicating the first distance L1 or the second distance L2 stored in the storage unit 152 and set the display region on the basis of the read information. For example, the information can be previously stored in the storage unit 152 while the first distance L1 is set as a value higher than or equal to 0 mm and lower than or equal to 3 mm, and the second distance L2 is set as a value higher than or equal to 30 mm, higher than or equal to 40 mm, or higher than or equal to 50 mm.

The computer 150 serving as a fourth unit may calculate the light fluence distribution information (light fluence spatial distribution) of the irradiation light inside the object 100 and set the display region on the basis of the calculated light fluence spatial distribution. For example, the computer 150 may calculate the light fluence spatial distribution inside the object 100 by solving a light diffusion equation represented by Expression (3).

[Math. 2]

$$\frac{1}{c}\frac{\partial}{\partial t}\Phi(r, t) = -\mu_a \Phi(r, t) + \nabla \cdot (D\nabla \Phi(r, t)) + S(r, t) \quad (3)$$

Where D denotes a diffusion coefficient, μ denotes an absorption coefficient, S denotes an incidence intensity of the irradiation light, φ denotes a reaching light fluence, r denotes a position, and t denotes time. Furthermore, the computer 150 may set a region where the light fluences in the calculated light fluence spatial distribution are within a predetermined range (for example, values higher than a predetermined threshold) as the display region. That is, the computer 150 may set a region where the light fluences in the calculated light fluence spatial distribution are out of the predetermined range (for example, values lower than the predetermined threshold) as the deep region 1030.

The computer 150 may also calculate a statistic value (such as a mean value or a median value) of the image value of the photoacoustic image data located at a certain distance from the surface of the object 100 with regard to a plurality of distances and evaluate those statistic values to set the display region. The computer 150 may set a region where the statistic values of the image values are within a predetermined numeric value range as the display region by using a correlation relationship that the generated sound pressure of the photoacoustic wave increases as the light thence increases. For example, the computer 150 may set a region where a mean value of the image values of the photoacoustic image data located at a certain distance from the surface of the object 100 is higher than a predetermined threshold as a region (display region) where the light fluences are high.

In addition, the image value in the display region set by the above-described method may be compared with the image value in a region except for the display region, and the display region may be set again by using a comparison result. For example, such a display region may be set that the statistic value (such as the mean value or the median value) of the image value in each of the regions or a ratio of the statistic values of the image values in the respective regions is within a predetermined numeric value range.

It should be noted that the display based on the display region determined by evaluating the image value of the photoacoustic image data may be performed first, and the user may manually set the display region again while the display image is checked by using the input unit 170.

In addition, a superimposed region of the display region set by the above-described method and a region of interest (ROI) set by another method may be updated as the display region. It should be noted that a method for the user to specify the ROI by using the input unit 170, a method of setting the ROI on the basis of the image data obtained by the other modality, and the like can be adopted as the setting method for the ROI. For example, the user may set the ROI with respect to the display image of the image data obtained by the other modality by using the input unit 170. The computer 150 can set the ROI in the photoacoustic image corresponding to the ROI in the display image obtained by the other modality.

S380: Step of Performing Rendering on Photoacoustic Image Data to be Displayed The computer 150 serving as a third unit performs rendering on the photoacoustic image data obtained in S350 to be displayed on the display unit 160 such that the display region set in S370 and the other region can be discriminated from each other.

For example, the computer 150 performs the rendering on the photoacoustic image data obtained in S350 such that the display region set in S370 is more emphasized than the other region to be displayed on the display unit 160. Specifically, the computer 150 may perform the rendering such that the opacity of the display region is set to be higher than that of the other region or the transparency of the display region is set to be lower than that of the other region. In addition, the rendering may be performed to emphasize the other region by decreasing the luminance in the region except for the display region at a certain rate. For example, a numeric value such as 0.2 times may be uniformly set as the rate for decreasing the luminance in the deep region 1030. The luminance in the region except for the display region may also be set by a correction table having a distribution of predetermined multiplying factors such as 0 to 1 time in accordance with the light fluence distribution or a distance in a depth direction. In addition, the computer 150 may perform the rendering such that the display region is emphasized by setting the display region as the rendering target and excluding the region except for the display region from the rendering target. At this time, the photoacoustic image data corresponding to the display region set as the rendering target may be projected by a related-art projection technique. For example, an arbitrary projection direction may be set, and a maximum intensity projection (MIP) image of a two-dimensional cross section may be displayed.

It should be noted that the rendering may be performed such that the region except for the object 100 is not emphasized by decreasing the opacity, decreasing the luminance, excluding the region from the rendering target, or the like with regard to the region except for the object 100 too.

The computer 150 may perform an analysis with respect to the photoacoustic image data corresponding to the display region and display an analysis result on the display unit 160. The analysis mentioned herein refers to statistic processing of a blood vessel density or the number of branches of blood vessels per unit area, a progress direction, an oxygen saturation, or the like.

In addition, the photoacoustic image data and the image data obtained by the other modality may be displayed such that the photoacoustic image data can be compared with the image data in a case where the image data obtained by the other modality also exists. For example, those pieces of image data may be compared and displayed by a display method by displaying the image data in parallel, superimposing, switching, or the like. Those pieces of image data may also be superimposed on each other while color maps are changed.

When the above-described display method is adopted, it is possible to display the rendering image in which the influence from the region where the reaching light fluences are low and the image quality decreases is suppressed. As a result, the user such as the doctor can check the rendering image where the high image quality region is selectively (preferentially) displayed and perform the diagnosis, and the diagnosis performance is improved.

Figure 6:
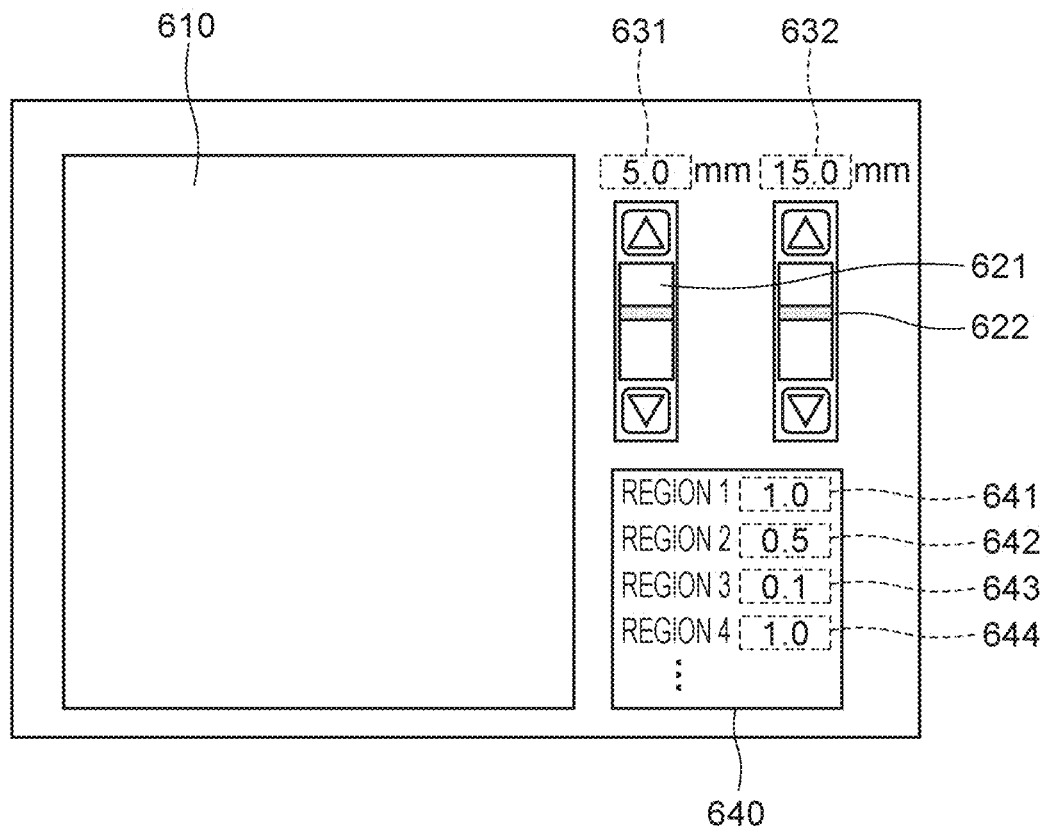
FIG. 6 is a schematic diagram illustrating a graphical user interface (GUI) according to the present exemplary embodiment.

Next, an example of a GUI that realizes the display method according to the present exemplary embodiment will be described. FIG. 6 is a schematic diagram of the GUI displayed on the display unit 160. The photoacoustic image data on which the rendering is performed in S380 is displayed in an image display area 610. When sliders in depth changing bars 621 and 622 are changed, it is possible to change distances in the depth direction for regulating the display region. That is, the depth changing bar 621 is a GUI with which a distance from the surface of the object 100 to a near surface of the display region (equivalent to the first distance L1) can be changed. The depth changing bar 622 is a GUI with which a distance from the surface of the object 100 to a far surface of the display region (equivalent to the second distance L2) can be changed. At this time, the set distances are displayed in depth display fields 631 and 632. The depth information set by the depth changing bar 621 is displayed in the depth display field 631. The depth information set by the depth changing bar 622 is displayed in the depth display field 632. The user may directly input the depth information (values of the distances) in the depth display fields 631 and 632 and use the depth display fields 631 and 632 as the GUIs with which the depth information can be changed. In addition, the input unit 170 such as a knob on external hardware or the like may be used as an input interface. The GUI illustrated in FIG. 6 includes a transparency display field 640 for specifying the transparencies of divided regions (the display region and the other region). The rendering is executed at the transparency of the region input in the transparency display field 640. A transparency display field 641 is a GUI for specifying and displaying the transparency of the region except for the object 100 (region 1). A transparency display field 642 is a GUI for specifying and displaying the transparency of a region (region 2) from the surface of the object 100 to the near surface of the display region. A transparency display field 643 is a GUI for specifying and displaying the transparency of the display region (region 3). A transparency display field 644 is a GUI for specifying and displaying the transparency of the deep region (region 4). In this manner, it is possible to specify the transparency of at least one region among the plurality of regions defined in S370 in the transparency display field 640. It should be noted that the GUI may also be configured such that the opacity of the region can be specified and displayed.

It should be noted that the GUI according to the present exemplary embodiment may be configured such that the other display parameter (such as the luminance) for the rendering in addition to the depth (distance) and the transparency can be changed.

In this manner, the display parameter (parameter for defining the display region, the transparency, or the like) is determined on the basis of the instruction of the user, and the rendering image is updated and displayed in accordance with the changed display parameter in the GUI according to the present exemplary embodiment. As a result, the user can set the desired display parameter while the rendering image in accordance with the display parameter is checked.

Next, the display region in the display method according to the present exemplary embodiment will be described.

Figure 7A:
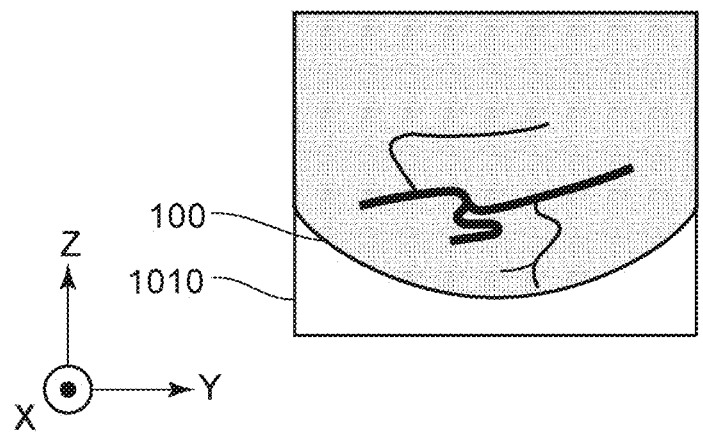
FIG. 7A is a schematic diagram illustrating various regions according to the present exemplary embodiment.

FIG. 7A is a schematic diagram of the photoacoustic image data as the reconstructed volume data in which the rectangular reconstruction region 1010 is set similarly as in FIG. 1A. The photoacoustic image data of FIG. 7A includes image data of the breast as the object 100. The photoacoustic image data illustrated in FIG. 7A is obtained when the breast is irradiated with light from the lower direction on paper.

Figure 7B:
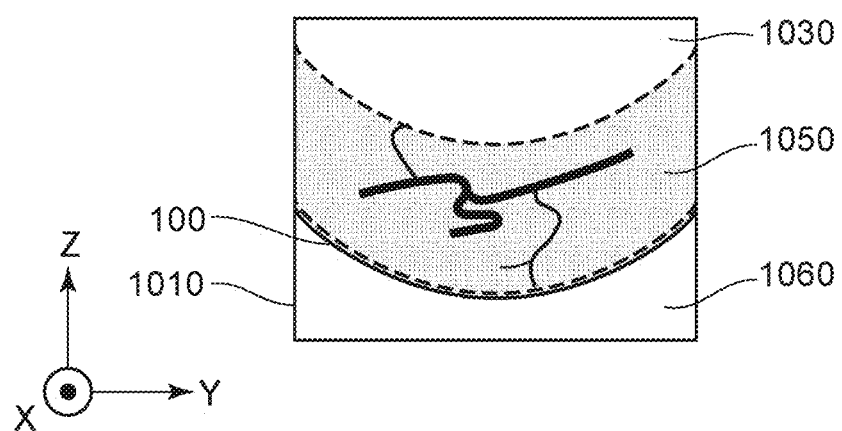
FIG. 7B is a schematic diagram illustrating the various regions according to the present exemplary embodiment.

As illustrated in FIG. 7B, the computer 150 can set the deep region 1030 away from the surface of the object 100 at a predetermined distance or farther on the basis of the positional information of the surface of the object 100 obtained in S360. In addition, it is possible to set the region 1060 except for the object 100 on the basis of the positional information of the surface of the object 100. In addition, the computer 150 can set the display region 1050 (region surrounded by a dotted line) which is not included in the deep region 1030 and the region 1060 except for the object 100 in the reconstruction region 1010. The computer 150 can perform the rendering on the photoacoustic image data to be displayed on the display unit such that the display region 1050 of FIG. 7B is more emphasized than the deep region 1030 and the region 1060 except for the object 100.

Figure 7C:
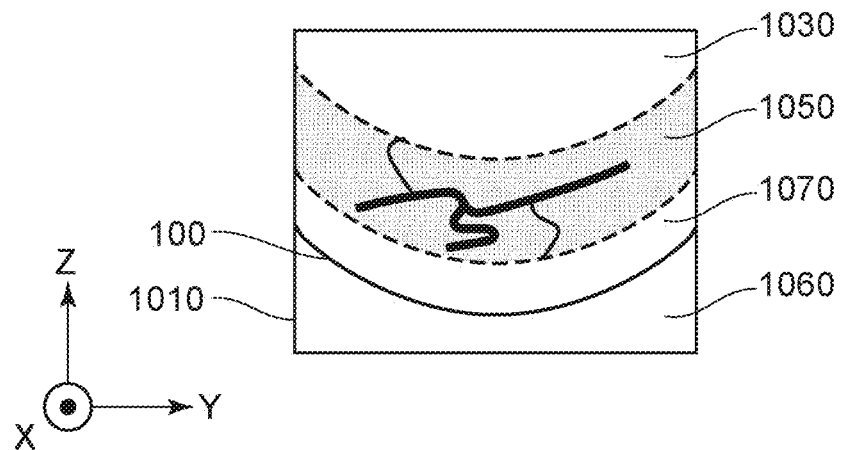
FIG. 7C is a schematic diagram illustrating the various regions according to the present exemplary embodiment.

The computer 150 can also the display region 1050 on the basis of the positional information of the surface of the object 100 as illustrated in FIG. 7C. That is, the computer 150 can set the region between the surface away from the surface of the object 100 by the first distance L1 and the surface away from the surface of the object 100 by the second distance L2 as the display region 1050. The computer 150 can also set the region 1060 except for the object 100 on the basis of the positional information of the surface of the object 100. In addition, the computer 150 can set a region (region in the vicinity of the surface of the object) 1.070 from the surface of the object 100 to the first distance L1 on the basis of the positional information of the surface of the object 100. Moreover, the computer 150 can set the display region 1050 (region surrounded by the dotted line) which is not included in the region 1060 except for the object 100 and the region 1070 in the vicinity of the surface of the object 100 in the reconstruction region 1010. The computer 150 can also perform the rendering on the photoacoustic image data to be displayed on the display unit such that the display region 1050 of FIG. 7B is more emphasized than the region 1060 except for the object 100 and the region 1070 in the vicinity of the surface of the object 100.

Figure 8A:
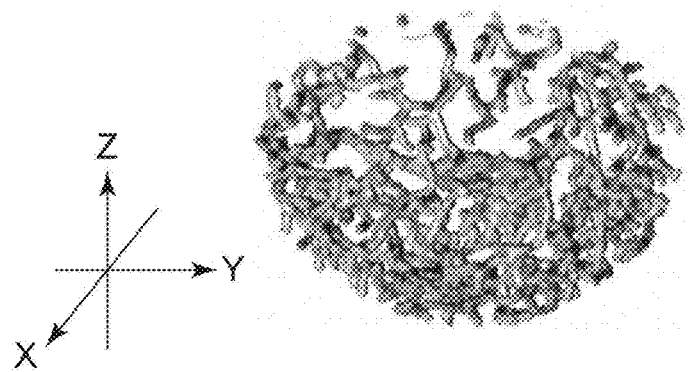
FIG. 8A is a schematic diagram illustrating a rendering image according to the present exemplary embodiment.

FIGS. 8A to SC are schematic diagrams of the rendering image three-dimensionally displayed by performing surface rendering on the photoacoustic image data of the various regions set as illustrated in FIGS. 7A to 7C. FIG. 8A illustrates the image after the surface rendering on a region where the object 100 exists (region excluding the region 1060 except for the object 100 from the reconstruction region 1010). This rendering image includes a blood vessel image existing in the region 1070 in the vicinity of the surface of the object 100, a noise image existing in the deep region 1030 of the object 100, and the like. In a case where the user desires to check the blood vessel image of the inside of the object 100, these images are unnecessary images, which may be impeditive to the diagnosis.

Figure 8B:
FIG. 8B is a schematic diagram illustrating the rendering image according to the present exemplary embodiment.
Figure 8C:
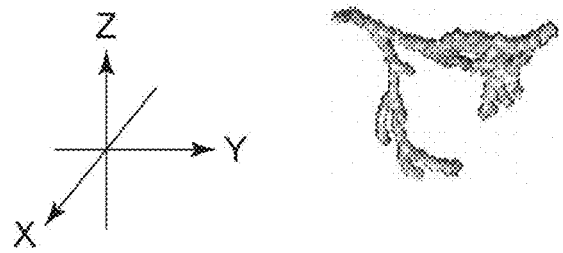
FIG. 8C is a schematic diagram illustrating the rendering image according to the present exemplary embodiment.

FIG. 8B illustrates an image obtained by selectively performing the surface rendering while the display region 1050 illustrated in FIG. 7B (region excluding the deep region 1030 of the object 100 and the region 1060 except for the object 100 from the reconstruction region 1010) is extracted. In FIG. 8B, the noise image existing in the deep region 1030 of the object 100 is excluded, and the visibility of the blood vessel image of the inside of the object 100 is improved as compared with FIG. 8A, FIG. 8C illustrates an image obtained by selectively performing the surface rendering while the display region 1050 illustrated in FIG. 7C (region excluding the deep region 1030 of the object 100, the region 1060 except for the object 100, and the region 1070 in the vicinity of the surface of the object 100 from the reconstruction region 1010) is extracted. In FIG. 8C, the blood vessel image existing in the region in the vicinity of the surface of the object 100 is also extracted in addition to the noise image existing in the deep region 1030 of the object 100. For this reason, the visibility of the blood vessel image of the inside of the object 100 is further improved as compared with FIG. 8B.

It should be noted that the visibility of the blood vessel image of the inside of the object 100 is improved in the image of FIG. 8C, but it becomes difficult to understand links of the blood vessels from the region in the vicinity of the surface of the object 100 to the inside. Therefore, the display of FIG. 8B and the display of FIG. 8C may be switched. That is, when the distance from the surface of the object 100 for defining the display region is set to be changeable, it is possible to perform the rendering in a display mode desired by the user.

In addition, images obtained by selectively performing the rendering on the various regions such as an object region where the object 100 exists, the display region 1050, the deep region 1030, the region 1060 except for the object 100, and the region 1070 in the vicinity of the surface may be switched and displayed. That is, the various regions may be set, and the display may be performed such that these regions can be discriminated from each other.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-233207, filed Nov. 30, 2016, which is hereby incorporated by reference herein in its entirety.

The invention claimed is:

1. A display control apparatus that performs rendering of volume data generated based on a signal obtained by receiving a photoacoustic wave generated by an object irradiated with light, the display control apparatus comprising:
    a first unit configured to obtain positional information of a first surface of the object;
    a second unit configured to set a display region inside the object between a second surface located at a first distance from the first surface of the object and a third surface located at a second distance from the first surface of the object, and set a surface vicinity region located from the first surface of the object to the second surface located at the first distance and set a deep region away from the third surface located at the second distance based on the first surface of the object; and
    a third unit configured to perform the rendering of the volume data in a manner that the display region is more emphasized than the surface vicinity region and the deep region,
    wherein the third unit performs the rendering of the volume data in a manner that an opacity of the display region is automatically set to be higher than an opacity of the surface vicinity region and the deep region, or a transparency of the display region is automatically set to be lower than a transparency of the surface vicinity region and the deep region, and
    wherein the third unit causes a display unit to display information about the first distance and information about the second distance together with an image on which rendering of volume has been performed.

2. The display control apparatus according to claim 1, wherein the third unit performs the rendering in a manner that the display region and the region except for the display region are set to have mutually exclusive transparencies or opacities.

3. The display control apparatus according to claim 1, wherein the third unit performs the rendering of the volume data without setting the region except for the display region as a rendering target.

4. The display control apparatus according to claim 1, wherein the first distance is not 0, and the second distance is higher than the first distance.

5. The display control apparatus according to claim 1, wherein the first unit obtains positional information of the first surface of the object based on the volume data.

6. The display control apparatus according to claim 5, wherein the first unit
    applies a smoothing filter to the volume data and generates the smoothed volume data, and
    defines a surface where a variation in image values of the smoothed volume data is within a predetermined range as the first surface of the object and obtains the positional information of the surface of the object.

7. The display control apparatus according to claim 1, wherein the second unit sets the display region defined by the second distance determined based on an instruction of a user.

8. The display control apparatus according to claim 1, further comprising:
    a fourth unit configured to obtain light fluence distribution information inside the object of the light with which the object is irradiated,
    wherein the second unit sets a region between the surface located at the first distance from the surface of the object and the surface located at the second distance from the surface of the object also corresponding to a region where light fluences are higher than a predetermined threshold as the display region based on the light fluence distribution information.

9. The display control apparatus according to claim 1, wherein the opacity of the display region is set higher or the transparency is set lower than the surface vicinity region and the deep region such that the display region is independently visually recognizable even though irradiation of the light attenuates as the distance to the first surface of the object increases.

10. A display method of performing rendering of volume data generated based on a signal obtained by receiving a photoacoustic wave generated by an object irradiated with light, the display method comprising:

obtaining positional information of a first surface of the object;

setting a display region inside the object between a second surface located at a first distance from the first surface of the object and a third surface located at a second distance from the first surface of the object, and set a surface vicinity region located from the first surface of the object to the second surface located at the first distance and set a deep region away from the third surface located at the second distance based on the first surface of the subject; and performing the rendering of the volume data in a manner that the display region is more emphasized than the surface vicinity region and the deep region, wherein the third unit performs the rendering of the volume data in a manner that an opacity of the display region is automatically set to be higher than an opacity of the surface vicinity region and the deep region, or a transparency of the display region is automatically set to be lower than a transparency of the surface vicinity region and the deep region, and wherein the third unit causes a display unit to display information about the first distance and information about the second distance together with an image on which rendering of the volume data has been performed.

11. A non-transitory storage medium that stores a program for causing a computer to execute the display method according to claim 10.

* * * * *